(12) United States Patent
Hawkes et al.

(10) Patent No.: US 10,137,214 B2
(45) Date of Patent: Nov. 27, 2018

(54) STERILIZATION CONTAINER WITH MOVABLE AND NESTABLE LID

(71) Applicant: Symmetry Medical Manufacturing, Inc., Warsaw, IN (US)

(72) Inventors: Jason Hawkes, Weare, NH (US); Robert Zeuge, Hooksett, NH (US)

(73) Assignee: SYMMETRY MEDICAL MANUFACTURING, INC., Warsaw, IN (US)

( * ) Notice: Subject to any disclaimer, the term of this patent is extended or adjusted under 35 U.S.C. 154(b) by 636 days.

(21) Appl. No.: 14/445,561

(22) Filed: Jul. 29, 2014

(65) Prior Publication Data

US 2016/0030617 A1 Feb. 4, 2016

(51) Int. Cl.
*B65D 43/16* (2006.01)
*A61L 2/26* (2006.01)

(52) U.S. Cl.
CPC ........... *A61L 2/26* (2013.01); *A61L 2202/182* (2013.01); *A61L 2202/24* (2013.01)

(58) Field of Classification Search
CPC ......... B65D 43/20; B65D 43/14; A45D 40/22
USPC ................... 220/810, 811, 244, 812
See application file for complete search history.

(56) References Cited

U.S. PATENT DOCUMENTS

| | | | |
|---|---|---|---|
| 391,145 A | 10/1888 | Hardin | |
| 2,112,451 A | 9/1938 | Best et al. | |
| 2,487,644 A * | 11/1949 | Frye | B60Q 7/005 217/7 |
| 3,342,343 A * | 9/1967 | Youlden | A47K 17/00 211/119.009 |
| 4,420,079 A | 12/1983 | Gliniorz et al. | |
| 5,411,134 A | 5/1995 | Temple et al. | |
| 5,520,313 A | 5/1996 | Toshihide | |
| 5,732,820 A * | 3/1998 | Tsai | B65D 43/20 206/369 |
| 6,264,027 B1 * | 7/2001 | Rhein | G11B 33/0411 206/308.1 |
| 6,470,627 B2 | 10/2002 | Fukuo | |
| 6,478,160 B1 | 11/2002 | Au et al. | |
| 6,669,023 B2 | 12/2003 | Kikuchi et al. | |
| 2001/0052524 A1 | 12/2001 | Ichimaru et al. | |
| 2009/0236257 A1 * | 9/2009 | Cross | B65D 43/164 206/540 |

* cited by examiner

*Primary Examiner* — Jeffrey Allen
(74) *Attorney, Agent, or Firm* — Hayes Soloway PC

(57) ABSTRACT

A sterilization container includes a floor. A first sidewall is connected to a first side of the floor and a second sidewall is connected to a second side of the floor wherein each of the first and second sidewalls has an elongated blind cavity formed along a length thereof. A first hinge is positioned partially within the blind cavity of the first sidewall, and a second hinge is positioned partially within the blind cavity of the second sidewall, wherein each of the first and second hinges are movable along a length of the first and second blind cavities, respectively. A lid is connected between the first and second hinges and is positionable between a first position substantially parallel with the floor on a third side of the floor, and a second position substantially parallel with the floor on a fourth side of the floor.

2 Claims, 8 Drawing Sheets

STERILIZATION CONTAINER WITH MOVABLE AND NESTABLE LID

FIELD OF THE DISCLOSURE

The present disclosure is generally related to containers and more particularly is related to a sterilization container with a movable and nestable lid.

BACKGROUND OF THE DISCLOSURE

Sterilization cases are used in the medical field to hold medical instruments. The medical instruments, when contaminated, are run through a sterilizer while held within a sterilization case. Sterilization cases are frequently used in settings where space is limited and compact and easy-to-use items come in handy. In this regard, sterilization cases with easy-to-use parts may be desired to heighten the efficiency of sterilizing medical instruments. In addition, it is a frequent occurrence for parts of sterilization cases, such as covers, to become separated from the cases when they're opened, resulting in the eventual disappearance of the part. This may render the sterilization case less effective, and may make the overall sterilization process less efficient.

Thus, a heretofore unaddressed need exists in the industry to address the aforementioned deficiencies and inadequacies.

SUMMARY OF THE DISCLOSURE

Embodiments of the present disclosure provide a sterilization container. Briefly described, in architecture, one embodiment of the system, among others, can be implemented as follows. A first sidewall is connected to a first side of a floor and a second sidewall connected to a second side of the floor, wherein the first side is opposite the second side, wherein each of the first and second sidewalls has an elongated blind cavity formed along a length thereof. A first hinge is positioned partially within the blind cavity of the first sidewall, and a second hinge is positioned partially within the blind cavity of the second sidewall, wherein each of the first and second hinges are movable along a length of the first and second blind cavities, respectively. A lid is connected between the first and second hinges, wherein the lid is positionable between at least a first position substantially parallel with the floor on a third side of the floor, and a second position substantially parallel with the floor on a fourth side of the floor, wherein the third side is substantially opposite the fourth side.

The present disclosure can also be viewed as providing methods of manufacturing a sterilization container. In this regard, one embodiment of such a method, among others, can be broadly summarized by the following steps: connecting a first sidewall to a first side of a floor; connecting a second sidewall to a second side of the floor, wherein the first side is opposite the second side, wherein each of the first and second sidewalls has an elongated blind cavity formed along a length thereof; positioning a first hinge partially within the blind cavity of the first sidewall; positioning a second hinge partially within the blind cavity of the second sidewall, wherein each of the first and second hinges are movable along a length of the first and second blind cavities, respectively; and connecting a lid between the first and second hinges, wherein the lid is positionable between at least a first position substantially parallel with the floor on a third side of the floor, and a second position substantially parallel with the floor on a fourth side of the floor, wherein the third side is substantially opposite the fourth side.

The present disclosure can also be viewed as providing a medical sterilization container having a hingedly fixed, slidable, and nestable lid. Briefly described, in architecture, one embodiment of the system, among others, can be implemented as follows. A first sidewall is connected to a first side of a floor and a second sidewall connected to a second side of the floor, wherein the first side is opposite the second side, wherein each of the first and second sidewalls has an elongated blind cavity formed along a length thereof, wherein the blind cavity has curvilinear terminating ends, wherein the floor is connected to the first and second sidewall along a lower portion of the first and second sidewalls. A tray insert is removably connectable between the first and the second sidewalls along a middle portion of the first and second sidewalls. A first hinge is positioned partially within the blind cavity of the first sidewall, and a second hinge is positioned partially within the blind cavity of the second sidewall, wherein each of the first and second hinges are movable along a length of the first and second blind cavities, respectively. A lid is connected between the first and second hinges, wherein the lid is positionable between at least a first position substantially parallel with the floor on a third side of the floor, and a second position substantially parallel with the floor on a fourth side of the floor, wherein the third side is substantially opposite the fourth side.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
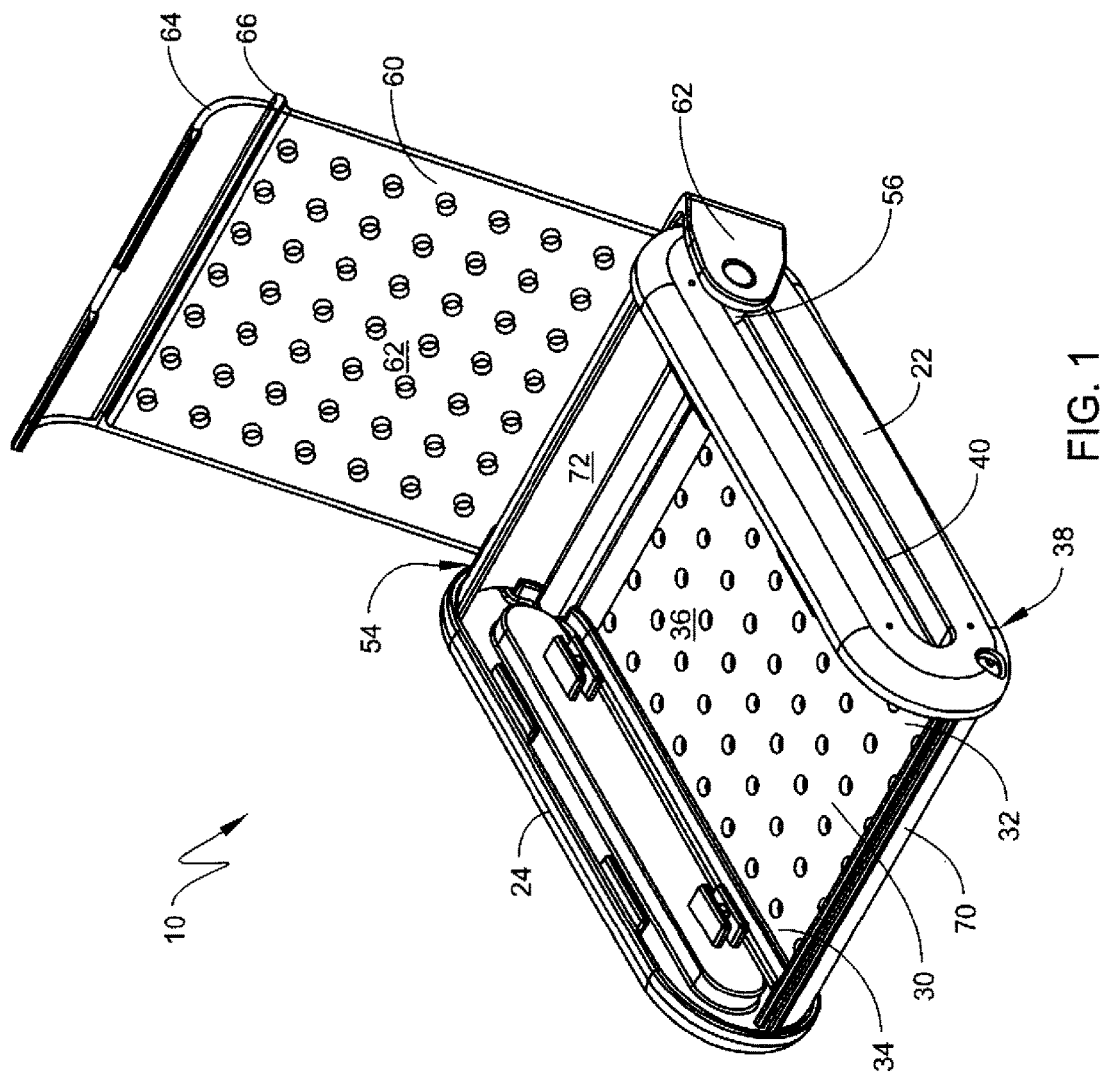
FIG. 1 is a cross-sectional illustration of a sterilization container, in accordance with a first exemplary embodiment of the present disclosure.

FIG. 1 is a cross-sectional illustration of a sterilization container 10, in accordance with a first exemplary embodiment of the present disclosure. The sterilization container 10 may be referred to herein as 'container 10' or 'apparatus 10.' A first sidewall 22 is connected to a first side 32 of a floor 30 and a second sidewall 24 connected to a second side 34 of the floor 30, wherein the first side 32 is opposite the second side 34, wherein each of the first and second sidewalls 22, 24 has an elongated blind cavity 40 formed along a length thereof. A first hinge 52 is positioned partially within the blind cavity 40 of the first sidewall 22, and a second hinge 54 is positioned partially within the blind cavity 40 of the second sidewall 24, wherein each of the first and second hinges 52, 54 are movable along a length of the blind cavities 40, respectively. A lid 60 is connected between the first and second hinges 52, 54, wherein the lid 60 is positionable between at least a first position substantially parallel with the floor 30 on a third side 36 of the floor 30, and a second position substantially parallel with the floor 30 on a fourth side 38 of the floor 30, wherein the third side 36 is substantially opposite the fourth side 38.

The container 10 may be used for holding medical instruments and implements before, during, and after a medical sterilization process. The sterilization process may sterilize the instruments with a sterilization material, such as water, steam, or another well-known sterilization material that penetrates through the container 10 via a plurality of holes to sterilize the instruments contained inside. The instruments may remain within the container 10 after the sterilization process and during a subsequent medical procedure. The container 10 may efficiently and conveniently hold the medical instruments for a medical practitioner during a procedure. The container 10 may utilize a lid 60 that can be moved between first and second positions, i.e., between a fully closed position and a fully open and nested position, thereby allowing the user of the container 10 greater convenience and efficiency than a conventional container with a fully removably lid.

The first and second sidewalls 22, 24 of the container 10 may be connected to the floor 30 to form the general structure of the container 10. The floor 30 may include a substantially planar structure constructed from a material used within the industry with conventional medical sterilization containers. Each of the first and second sidewalls 22, 24 may extend upwards from the floor 30, and may be connected with a front plate 70 and/or a back plate 72, among other structures. The front plate 70 and back plate 72 may help retainer the container 10 together to create a substantially unitary structure. The first and second sidewalls 22, 24 may have a substantially elongated shape with curvilinear terminating ends, and the front plate 70 and back plate 72 may also include matching contours or shapes to the curvilinear ends of the first and second sidewalls 22, 24.

The blind cavity 40 of each of the first and second sidewalls 22, 24 may be formed within the first and second sidewalls 22, 24, such that an opening of the blind cavity 40 is substantially aligned with an exterior surface of the first and second sidewalls 22, 24 and an interior floor of the blind cavity 40 is positioned interior of the exterior surface. Thus, the opening of the blind cavities 40 may be oppositely facing the floor 30 connected between the first and second sidewalls 22, 24. The specific dimensions, shape, and orientation of the blind cavity 40 may vary, depending on the design of the container 10. For example, the blind cavity 40 may be positioned substantially along a length of the first and second sidewalls 22, 24 and may terminate at opposing ends of the first and second sidewalls 22, 24 in a position before the curvilinear ends of the first and second sidewalls 22, 24. The terminating ends of the blind cavity 40 may also be curvilinear.

The first and second hinges 52, 54 may be positioned partially within the blind cavity 40 of the first and second sidewalls 22, 24. Specifically, the hinges 52, 54 may each have a cavity engagement protrusion 56, among other parts, that are sized to be received within the blind cavity 40. The hinges 52, 54 may extend from the engagement protrusion 56 across an exterior surface of the first and second sidewalls 22, 24. The hinges 52, 54 may be angled back toward an interior of the container 10 such that they can be positioned for attachment to the lid 60, as will be described in further detail.

In use, the hinges 52, 54 may move in unison and be slidable along the length of the blind cavity 40 of each of the first and second sidewalls 22, 24. When the hinges 52, 54 are positioned at a terminating end of the blind cavity 40, they may be rotated such that the distal end of each of the hinges 52, 54 traverses around the terminating end of the first and second sidewalls 22, 24, respectively. This motion may allow the lid 60 attached between the hinges 52, 54 to slide along the container 10 and rotated relative to the container 10. Further, as will be described in greater detail, the lid 60 may be rotated to a point where it is substantially parallel to the floor 30 and can be slid under the floor 30, such that it is positioned abutting to the fourth side 38 of the floor 30.

The lid 60 may be a structure that has a substantially planar main portion 62 and a curvilinear portion 64 connected to a side of the main portion 62. Each of the first and second sidewalls 22, 24 having an elongated length with terminating ends at opposing sides of the elongated length, may include curvilinear terminating ends which are substantially equal to the curvature of at least a portion of the curvilinear portion 64 of the lid 60. Thus, when the lid 60 is in a fully closed position, the curvilinear portion 64 may be substantially aligned with an outline of the curvilinear ends of the first and second sidewalls 22, 24. When the lid 60 is positioned in the first position, i.e., the fully closed position, an exterior surface of the lid 60 may be positioned substantially aligned with an exterior edge of each of the first and second sidewalls 22, 24. When the lid 60 is positioned in the second position, i.e., the fully open and nested position, an exterior surface of the lid 60 may be positioned substantially aligned with an exterior edge of each of the first and second sidewalls 22, 24.

The lid 60 may also include a handle 66 positioned thereon. The handle 66 may be positioned between the substantially planar main portion 62 and the curvilinear portion 64. While the handle 66 may allow a user to open the lid 60 from the closed position, the handle 66 may also act as a base for the container 10 along with the hinges 52, 54 when the lid is in the fully nested position. For example, when the lid 60 is in the second position, e.g., the fully nested position, a distance between a terminating end of the handle 66 and an exterior face of the lid 60 may be substantially equivalent to a distance between an exterior side of each of the first and second hinges 52, 54 and the exterior face of the lid 60. This configuration may allow the container 10 to sit flat on a surface, such as a table.

In accordance with this disclosure, the curvilinear shape of the components of the container 10 may include various curves, angles, and arcs, including those with constant radii. The specific shape of the curvilinear component parts may be selected based on interaction of the various container 10 components. For example, the shape and size of the curvilinear ends of the first and second sidewalls 22, 24 may be selected based on a size of the first and second hinges 52, 54, such that the hinges 52, 54 are capable of rotating around the terminating end of the first and second sidewalls 22, 24.

Figure 2:
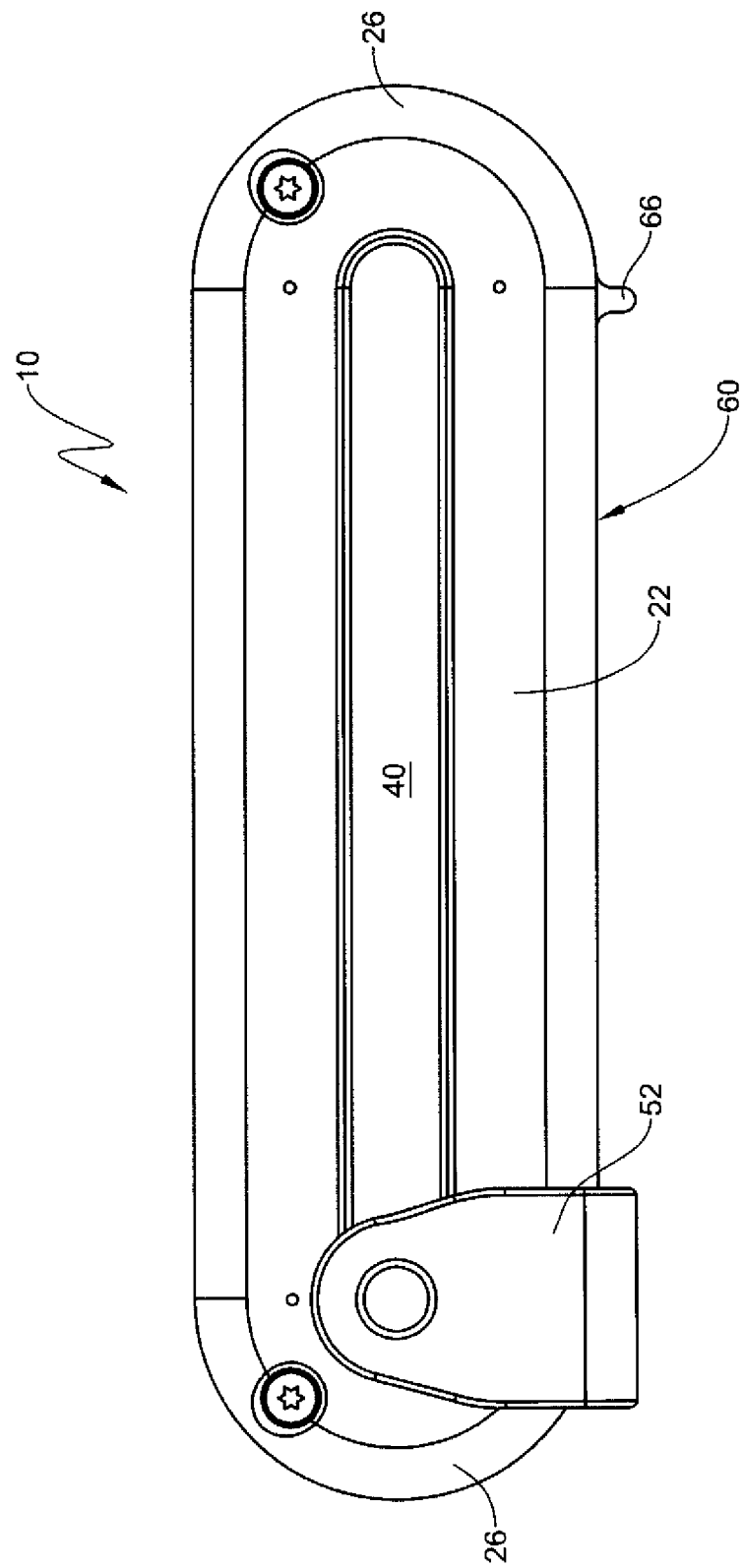
FIG. 2 is a side view illustration of the sterilization container of FIG. 1, in accordance with the first exemplary embodiment of the present disclosure.

FIG. 2 is a side view illustration of the sterilization container 10 of FIG. 1, in accordance with the first exemplary embodiment of the present disclosure. As is shown in FIG. 2, the blind cavity 40 of each of the first and second sidewalls 22, 24 may be formed with the opening of the blind cavity 40 substantially aligned with an exterior surface of the first and second sidewalls 22, 24. The interior floor of the blind cavity 40 is positioned interior of the exterior surface. The blind cavity 40 may extend substantially along the length of the first and second sidewall 22, 24, thereby allowing the first and second hinge 52, 54 to move along the length of the first and second sidewall 22, 24 and around a terminating end 26 of the first and second sidewall 22, 24. In FIG. 2, the lid 60 is shown in the fully open and nested position, with the lid 60 being positioned substantially under the container 10. As can be seen, the handle 66 of the lid 60 is shown extending down from the container 10, such that a terminating end of the handle 66 is positioned a substantially equivalent distance from the container 10 floor as the hinges 52, 54. Also shown in FIG. 2 are a plurality of threaded fasteners 80 or similar structures which are engaged between the first and second sidewall 22, 24 and the front plate 70 and back plate 72 (FIG. 1).

Figure 3:
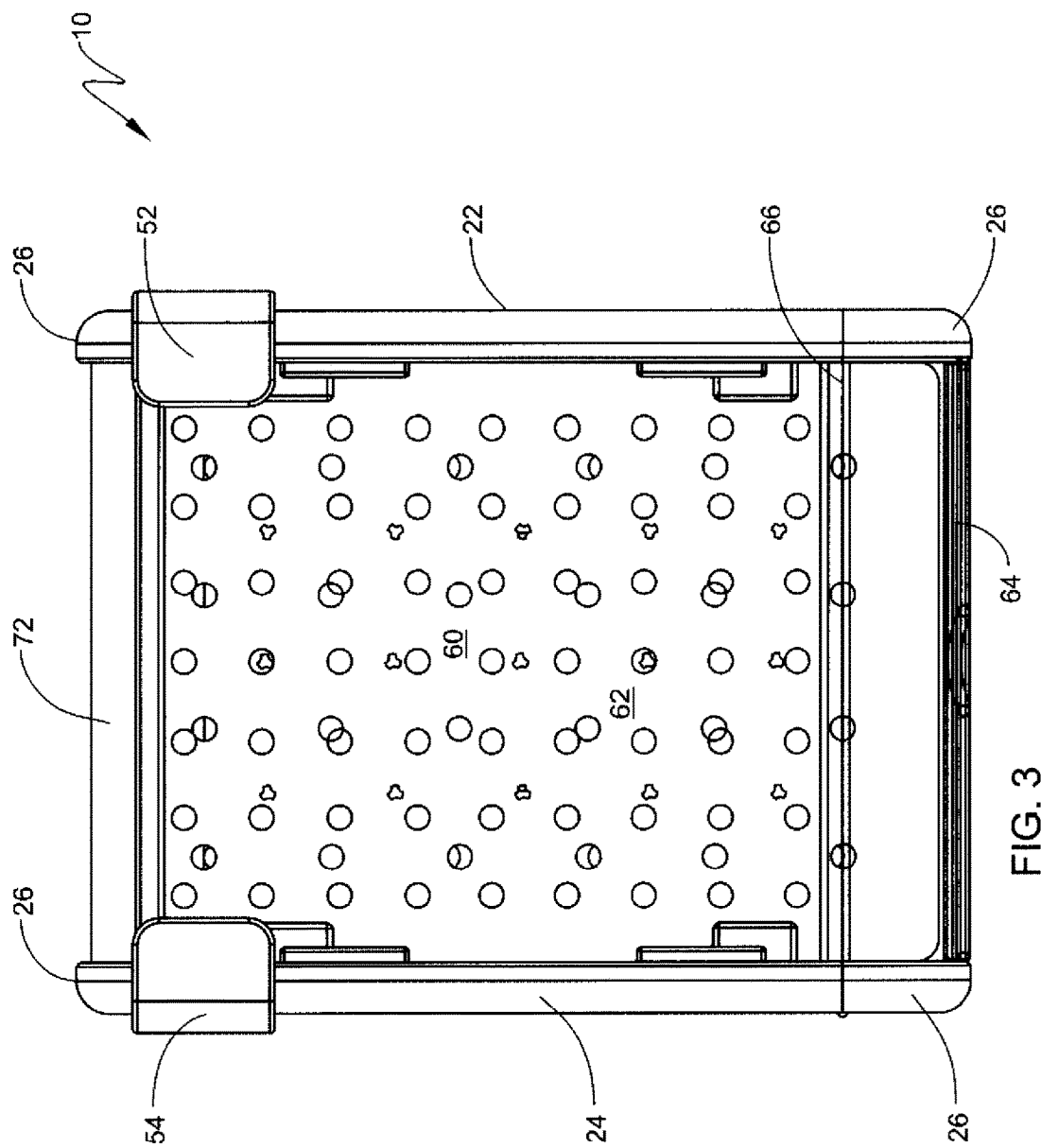
FIG. 3 is a top view illustration of the sterilization container of FIG. 1, in accordance with the first exemplary embodiment of the present disclosure.

FIG. 3 is a top view illustration of the sterilization container 10 of FIG. 1, in accordance with the first exemplary embodiment of the present disclosure. As is shown in FIG. 3, the lid 60 of the container 10 is shown in the fully closed position, with the lid 60 covering the top of the container 10. The back plate 72 may be positioned between the first and second sidewalls 22, 24 such that it is inset into the container 10. As the lid 60 is moved around the terminating ends 26 of the first and second sidewalls 22, 24, the inset positioning of the back plate 72 may allow the lid 60 to move around the terminating ends 26.

In using the container 10, FIG. 3 depicts the container 10 having the lid 60 fully closed, which may correspond to a situation where the container is currently storing medical instruments. For example, the medical instruments may be stored within an interior compartment of the container 10 with the lid 60 fully closed when the instruments are being stored, being sterilized, or being prepared for a medical operation.

Figure 4:
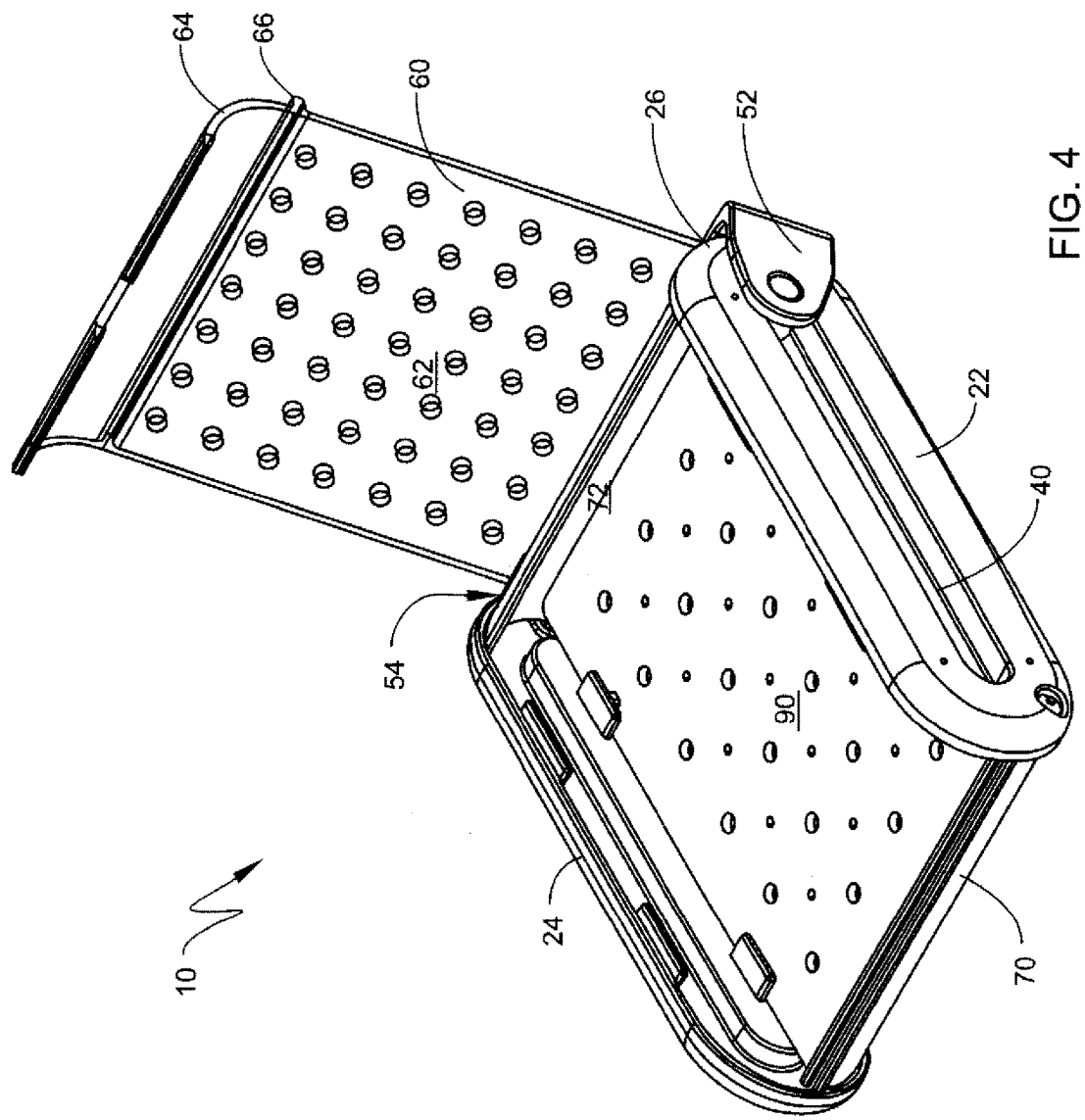
FIG. 4 is a top plan view illustration of the sterilization container of FIG. 1, in accordance with the first exemplary embodiment of the present disclosure.

FIG. 4 is a top plan view illustration of the sterilization container 10 of FIG. 1, in accordance with the first exemplary embodiment of the present disclosure. FIG. 4 depicts the container 10 with the lid 60 in the partially opened position, such as where the lid has been retracted from the fully closed position of FIG. 3. As can be seen from FIGS. 3-4, the hinges 52, 54 have been moved along the first and second sidewalls 22, 24 and are positioned along the terminating ends 26 thereof. This position of the hinges 52, 54 may place the lid 60 in a substantially perpendicular position relative to a length of the first and second sidewalls 22, 24, such that the curvilinear portion 64 of the lid and the handle 66 are positioned extended from the container 10 body. The curvilinear shape of the terminating ends 26 of the first and second sidewalls 22, 24 may allow for a smooth and fluid movement of the hinges 52, 54 between positions. Also shown in FIG. 4 is a tray insert 90 positioned within the container 10 above the floor 36, and connected between the first and second sidewalls 22, 24.

Figure 5:
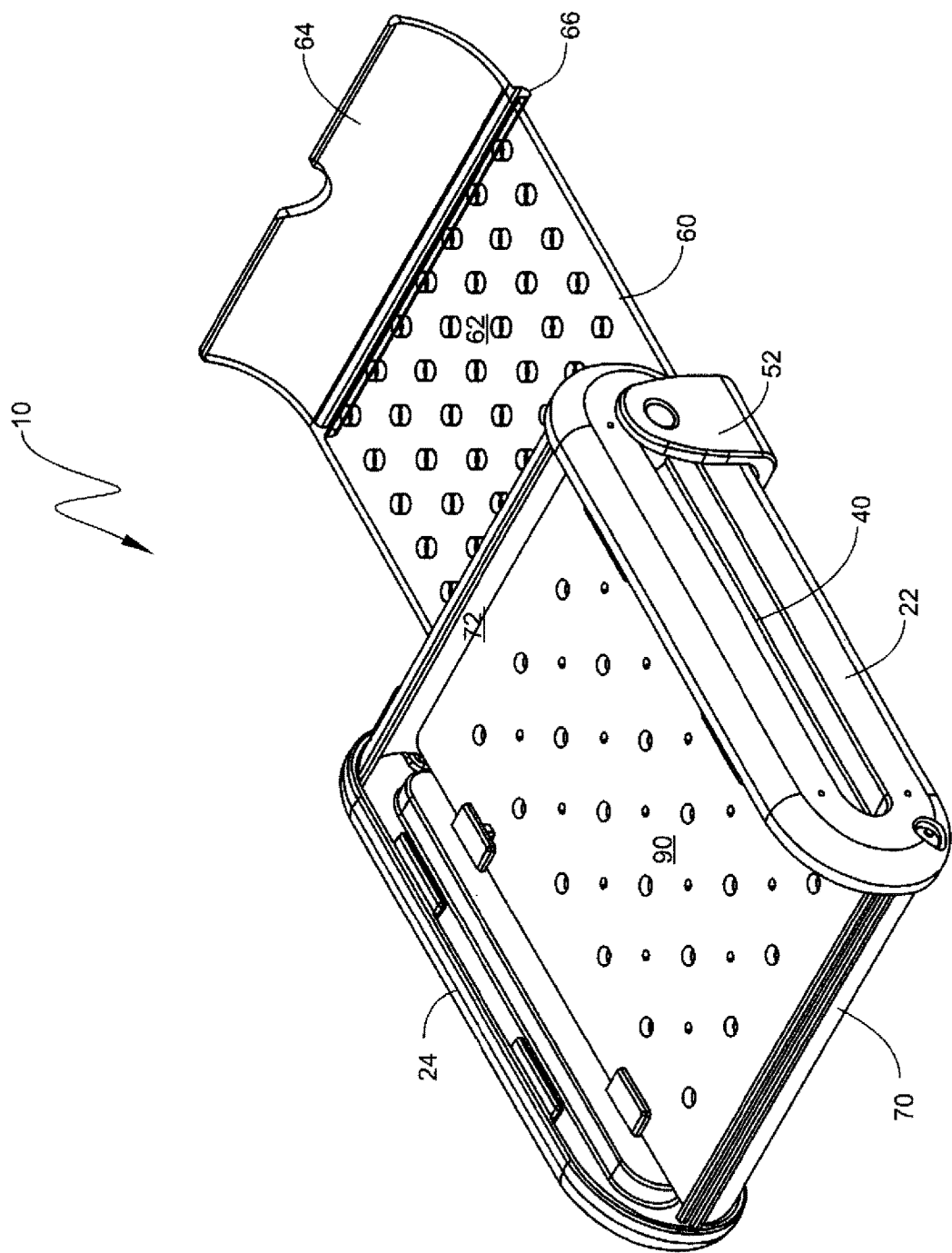
FIG. 5 is a top plan view illustration of the sterilization container of FIG. 1, in accordance with the first exemplary embodiment of the present disclosure.

FIG. 5 is a top plan view illustration of the sterilization container 10 of FIG. 1, in accordance with the first exemplary embodiment of the present disclosure. As is shown in FIG. 5, the lid 60 is positioned in the fully opened position in an orientation where the lid 60 is substantially parallel to the floor 36. In this position, the lid 60 is situated to be retracted under the container 10 and into a nested position. Compared to FIGS. 3-4, the position of the hinges 52, 54 in FIG. 5 are below the first and second sidewalls 22, 24, such that the cavity engagement protrusion 56 of each hinge 52, 54 can be slid along the cavity 40 when the lid 60 is retracted.

Figure 6:
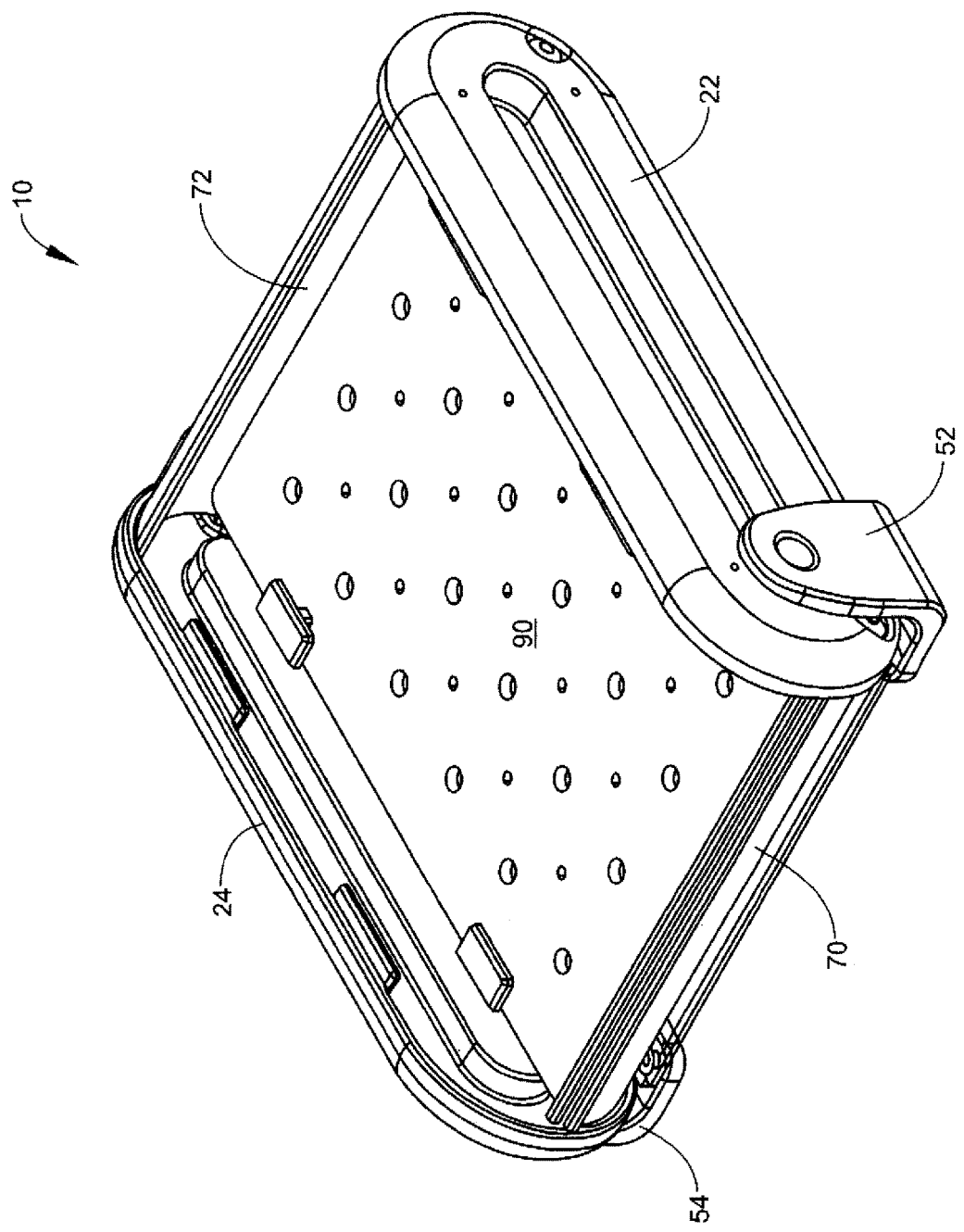
FIG. 6 is a top plan view illustration of the sterilization container of FIG. 1, in accordance with the first exemplary embodiment of the present disclosure.

FIG. 6 is a top plan view illustration of the sterilization container 10 of FIG. 1, in accordance with the first exemplary embodiment of the present disclosure. As is shown in FIG. 6, the lid 60 (FIG. 5) is positioned in the fully retracted or nested position, such that it is positioned under the container 10. Compared to FIGS. 3-5, the hinges 52, 54 are now positioned along an underside of the first and second sidewall 22, 24 and proximate to the front plate 70. In this position, the lid 60 may be positioned substantially parallel to the floor 36 (FIG. 1), and the sterilization tray insert 90. The curvilinear portion of the lid 60 (not visible) may be positioned abutting the back plate 72. In use of the container 10, the fully nested position of FIG. 6 may correspond to a situation where the container 10 is being used during a medical procedure to provide medical instruments and the lid 60 is efficiently stowed away.

Figure 7:
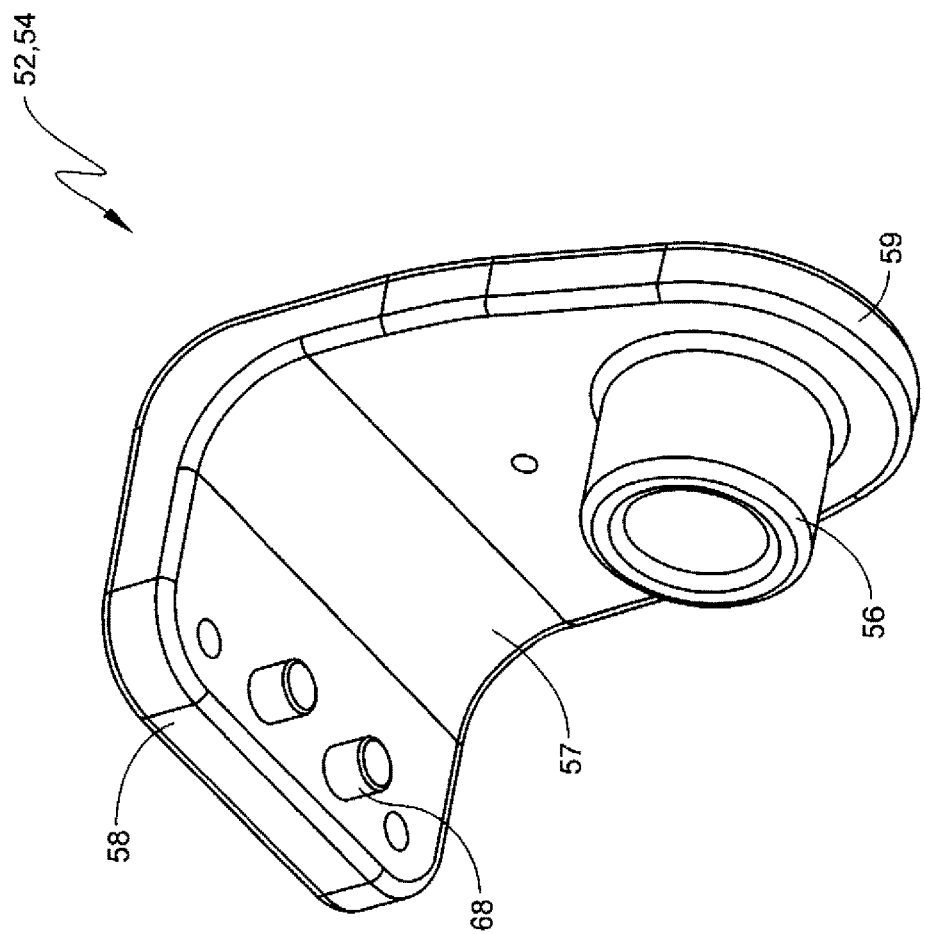
FIG. 7 is a plan view illustration of the hinges of the sterilization container of FIG. 1, in accordance with the first exemplary embodiment of the present disclosure.

FIG. 7 is a plan view illustration of the hinges 52, 54 of the sterilization container 10 of FIG. 1, in accordance with the first exemplary embodiment of the present disclosure. As can be seen in FIG. 7, the hinges 52, 54, may each have an angled bracket 57 having at least two ends 58, 59. The two ends 58, 59 may be positioned substantially perpendicular to one another. A cavity engagement protrusion 56 may be positioned on a first 59 of the two ends 58, 59 and a lid engagement structure 68 may be positioned on a second 58 of the two ends 58, 59. The lid engagement structure 68 may engage or connect to the lid 60 (FIGS. 1-6) while the cavity engagement protrusion 56 may engage with the blind cavity 40 (FIG. 1). The shape and angle of the bracket 57 may allow the first end 59 to constantly abut either the first or second sidewall 22, 24, while the second end 58 carries the lid 60 between a top and bottom of the container 10 and about the terminating ends of the first and second sidewalls 22, 24. A distance between the cavity engagement protrusion 56 and a surface of the second end 58 of the two ends 58, 59 may be substantially equivalent to a distance from a point on the elongated blind cavity to an edge of the first and second sidewall 22, 24, respectively.

Figure 8:
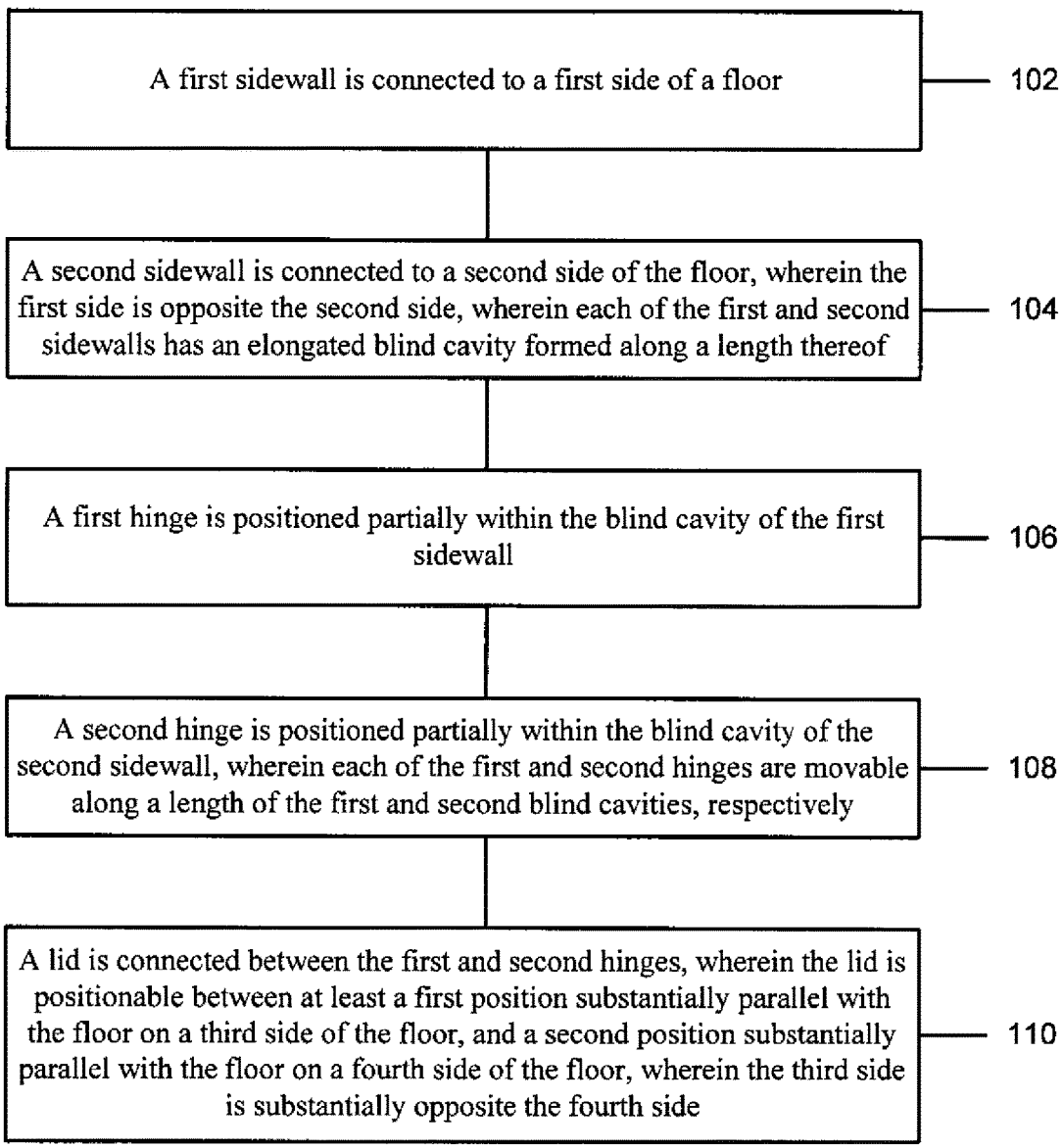
FIG. 8 is a flowchart illustrating a method of manufacturing a sterilization container in accordance with a second exemplary embodiment of the disclosure.

FIG. 8 is a flowchart 100 illustrating a method of manufacturing a sterilization container in accordance with a second exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 102, a first sidewall is connected to a first side of a floor. A second sidewall is connected to a second side of the floor, wherein the first side is opposite the second side, wherein each of the first and second sidewalls has an elongated blind cavity formed along a length thereof (block 104). A first hinge is positioned partially within the blind cavity of the first sidewall (block 106). A second hinge is positioned partially within the blind cavity of the second sidewall, wherein each of the first and second hinges are movable along a length of the first and second blind cavities, respectively (block 108). A lid is connected between the first and second hinges, wherein the lid is positionable between at least a first position substantially parallel with the floor on a third side of the floor, and a second position substantially parallel with the floor on a fourth side of the floor, wherein the third side is substantially opposite the fourth side (block 110). Any number of other steps, processes, or functions may be included with the method, including any functions disclosed herein.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A sterilization container comprising:
    a floor;
    a first sidewall connected to a first side of the floor and a second sidewall connected to a second side of the floor, wherein the first side is opposite the second side, wherein each of the first and second sidewalls has an elongated blind cavity formed along a length thereof;
    a first hinge positioned partially within the blind cavity of the first sidewall, and a second hinge positioned partially within the blind cavity of the second sidewall, wherein each of the first and second hinges are movable along a length of the first and second blind cavities, respectively; and
    a lid connected between the first and second hinges, wherein the lid is positionable between at least a first position substantially parallel with the floor on a third side of the floor, and a second position substantially parallel with the floor on a fourth side of the floor, wherein the third side is substantially opposite the fourth side, wherein the lid and the floor each define a plurality of holes adapted to allow a sterilization fluid to pass therethrough;
    further comprising a membrane tray insert positioned between the first and second sidewalls, wherein the membrane tray insert is connected to each of the first and second sidewalls.

2. A medical sterilization container having a hingedly fixed, slidable, and nestable lid, the medical sterilization container comprising:
    a floor;
    a first sidewall connected to a first side of the floor and a second sidewall connected to a second side of the floor, wherein the first side is opposite the second side, wherein each of the first and second sidewalls has an elongated blind cavity formed along a length thereof, wherein the blind cavity has curvilinear terminating ends, wherein the floor is connected to the first and second sidewall along a lower portion of the first and second sidewalls;
    a tray insert removably connectable between the first and the second sidewalls along a middle portion of the first and second sidewalls;
    a first hinge positioned partially within the blind cavity of the first sidewall, and a second hinge positioned partially within the blind cavity of the second sidewall, wherein each of the first and second hinges are movable along a length of the first and second blind cavities, respectively; and
    a lid connected between the first and second hinges, wherein the lid is positionable between at least a first position substantially parallel with the floor on a third side of the floor, and a second position substantially parallel with the floor on a fourth side of the floor, wherein the third side is substantially opposite the fourth side, wherein the lid and the floor each define a plurality of holes adapted to allow a medical sterilization fluid to pass therethrough.

* * * * *